(12) United States Patent
Senn et al.

(10) Patent No.: US 7,104,793 B2
(45) Date of Patent: Sep. 12, 2006

(54) LIGHT POLYMERIZATION DEVICE

(75) Inventors: Bruno Senn, Buchs (CH); Wolfgang Plank, Rankweil (AT)

(73) Assignee: Ivoclar Vivadent AG, Schaan (LI)

( * ) Notice: Subject to any disclaimer, the term of this patent is extended or adjusted under 35 U.S.C. 154(b) by 72 days.

(21) Appl. No.: 10/648,465

(22) Filed: Aug. 25, 2003

(65) Prior Publication Data

US 2004/0224280 A1  Nov. 11, 2004

(30) Foreign Application Priority Data

May 6, 2003  (DE) ................... 103 20 141

(51) Int. Cl.
  *A61C 3/00*  (2006.01)
  *A61C 5/00*  (2006.01)
(52) U.S. Cl. ........................ 433/29; 362/373
(58) Field of Classification Search .................. 433/29, 433/215, 216, 32; 362/572, 573, 580, 373; 606/1, 13, 16; 607/88; 34/96, 97
See application file for complete search history.

(56) References Cited

U.S. PATENT DOCUMENTS

| | | | | |
|---|---|---|---|---|
| 3,418,452 A | * | 12/1968 | Grabner | ...................... 392/383 |
| 3,712,984 A | * | 1/1973 | Lienhard | ................. 250/504 H |
| 4,149,086 A | * | 4/1979 | Nath | ....................... 250/504 R |
| 4,298,806 A | * | 11/1981 | Herold | .................... 250/504 H |
| 5,029,957 A | * | 7/1991 | Hood | ........................... 385/27 |
| 5,471,129 A | | 11/1995 | Mann | |
| 5,530,632 A | * | 6/1996 | Shikano et al. | ............. 362/109 |
| 5,634,711 A | * | 6/1997 | Kennedy et al. | ............ 362/119 |
| 2002/0136028 A1 | * | 9/2002 | Smith | ......................... 362/580 |
| 2002/0151941 A1 | * | 10/2002 | Okawa et al. | ................ 607/99 |
| 2004/0029069 A1 | * | 2/2004 | Gill et al. | ..................... 433/29 |
| 2004/0185413 A1 | * | 9/2004 | Gill et al. | ..................... 433/29 |

FOREIGN PATENT DOCUMENTS

DE  34 11 996 A1  10/1985

* cited by examiner

*Primary Examiner*—Todd E. Manahan
(74) *Attorney, Agent, or Firm*—John C. Thompson; Alan S. Korman

(57) ABSTRACT

A light polymerization device particularly suitable for the polymerization of dental material. The device includes a housing, a fan installed in the housing, the fan being in particular an axial fan, and a light source which emits polymerization radiation. The rotational axis of the fan extends transversely to the emission axis of the light source, and the air outlet of the fan can be on a side of the housing.

18 Claims, 5 Drawing Sheets

LIGHT POLYMERIZATION DEVICE

CROSS-REFERENCE TO RELATED APPLICATIONS

This application claims foreign priority benefits under 35 U.S.C. §119 from German patent application Ser. No. 103 20 141.6 filed May 6, 2003.

TECHNICAL FIELD

The present invention relates to a light polymerization device, and more particularly to a light polymerization device for polymerizing dental materials.

BACKGROUND OF THE INVENTION

Light polymerization devices of the type which are operated as hand-held devices typically include a substantially strong light radiation source which emits light radiation that subsequently passes through a light guide, such light polymerization devices serving to polymerize dental materials. The light radiation source is, typically, a light source which is also, however, partially a heat source, whereby the term "light" also comprises ultraviolet radiation.

Such light sources and light radiation sources typically give off heat in the form of heat loss, which must be conducted away from the decidedly compact hand-held device.

In fact, it has already been suggested to provide substantially large cooling ribs around the light source and to rely upon natural convection to ensure the conducting away of heat.

It is precisely with respect to high performance halogen light sources, however, that a cooling approach of this type is not sufficient, whereby, in all such cases, a cooling operation by a fan is provided.

In the prior art, such a fan cooling involves an axial fan deployed for the cooling, whose dimensions are selected in correspondence with the diameter of the housing of the hand-held device so that the cooling air stream flows through the hand-held device substantially parallel to the longitudinal axis thereof. Since it would not be acceptable for a fan to blow air onto the patient treatment location, the air outlet is most often provided on the back side of the housing.

DE-OS 34 11 996 discloses an approach to prevent the result that the fan directly blows onto the dentist applying the treatment or, as the occasion arises, onto the attending dental technician, wherein the air outlet is somewhat downwardly inclined so that the cooling airflow at least is not directed toward the face of the dentist or the dental technician.

The heretofore conventional light polymerization devices having forced cooling characteristically produce, across the full range of such products, an airflow from the patient to the dentist. This means, however, on the one hand, that a significant risk of infection exists for the dentist; at the least, the exhalations of the patient are directly guided toward the dentist.

In order to reduce the risk of infection somewhat, many dentists wear a mouth protector at least during the time of the light polymerization device treatment. This, however, is frequently perceived as unpleasant so that this precautionary measure is, in many instances, not undertaken.

A further problem is the creation of noise from the hand-held device due to the fan operation. With respect to a hand-held device, compact dimensions are desired. Correspondingly, there remains only a decidedly small gap available for the fan airflow. A particular problem is the reflector associated with the light source of the light polymerization device. The reflector has a conventionally known conical form and its outer diameter is only somewhat relatively smaller than the inner diameter of the housing.

At the particular location of the reflector, only a small annular gap is available which thus raises the necessity of a high flow velocity and, consequently, the creation of a comparatively large noise condition. Moreover, a substantially strong fan must be deployed in order to achieve a sufficient cooling in spite of this flow resistance. This fan brings with it not only the necessity of a rapid discharge of the storage battery power supply but, additionally, brings with it the generation of a decidedly strong noise condition.

In order, nonetheless, to make possible a practical working time, it is disclosed in U.S. Pat. No. 5,471,129 to use a substantially large storage battery power supply which, at the same time, is user-friendly in that it lowers the center of mass of the hand-held device, the storage battery power supply being received in the pistol grip of the hand-held device.

Such an approach, in fact, reduces the disadvantage of shortened storage battery power supply time associated with other conventional light polymerization device hand-held devices. The hand-held device is, however, significantly heavy and, consequently, less amenable to a user-friendly hand-held device operation.

A further problem of the known light polymerization devices, which is linked with the afore-described problems, lies in the comparatively reduced effective cooling efficiency. While the cooling air passing through the annular gap around the reflector—that is, around the outer circumference of the reflector—exhibits a substantially high flow velocity, the respective flow velocity and, consequently, the respective cooling effectiveness, is lower at precisely the location of the highest temperature—namely, in the vicinity of the filament.

In order to compensate for this disadvantageous impact, two measures had been suggested: on the one hand, cooling ribs for the cooling body have been extended around the entire reflector so that they reach even to the annular gap. This approach improves, in fact, the cooling effectiveness substantially but, however, requires the production of a difficult to manufacture and comparatively heavy reflector.

The other approach provides for a reduction in the flow cross-section in the region of the filament—namely, on the back side of the reflector. In this manner, the flow velocity is also comparatively high at that location and an improved cooling is possible. A disadvantage of this approach is, however, that the flow resistance in total increases still further so that, while the cooling effectiveness improves, the flow resistance also, however, increases.

OBJECTS AND SUMMARY OF THE INVENTION

The present invention provides a solution to the challenge of providing a light polymerization device which reduces the risk of infection for dentists, in view of its capability to be operated in a hand-held mode due to its improved comparatively reduced storage battery power supply weight, and which offers a reduced noise level while, however, offering the possibility of manufacturing the device at a reduced manufacturing cost.

The inventive approach provides that the cooling air stream is configured transverse to the housing of the light polymerization device. In this connection, it is to be understood that the term "housing" comprises the actual housing—that is, the housing without the hand grip.

The cooling airflow preferably extends precisely past the socket of the light source—that is, from one side of the housing to an opposed side of the housing. The cooling airflow is clearly shorter than the cooling airflow of the conventionally known hand-held devices; for example, a fourth or a third of the length of such conventional cooling airflow lengths. The flow velocity can be likewise dramatically reduced to, for example, one-third of the conventional flow velocity. The cooling body can be substantially easier to configure and manufacture in that it alone forms the sole noteworthy flow resistance. The cooling occurs directly at the location at which the heat loss occurs-that is, at the light source.

The cooling ribs extend in a conventionally known matter parallel to the cooling flow. Due to the fact that this cooling flow is, however, turned through a right angle relative to the orientation of the conventional cooling streams, the cooling ribs extend likewise in an orientation which is turned approximately ninety degrees relative to the conventional cooling rib orientation.

In accordance with the present invention, it is particularly advantageous if an arrangement for intensive conducting of heat is provided between the light source and the decidedly small cooling body.

The arrangement for intensive conducting of heat can either be provided in a direct configuration—that is, the light source directly connected with the cooling body—or can be provided in an indirect configuration. In this indirect configuration, the light source is disposed in a good heat conducting disposition with the socket and/or the reflector and, in turn, the socket and/or the reflector is connected to the cooling body. It is to be understood that care should be taken that, precisely in connection with an indirect heat conducting arrangement, the heat transfer resistance remains low.

In connection with the use of a halogen light source with integrated reflectors, it is advantageous, in accordance with the present invention, if the heat conducting capability between the filament and the cooling body is the most effective possible. In this connection, for example, the socket of the halogen light source can be disposed in good heat conducting relation to the cooling body. It is also possible to dimension the cooling body such that the terminal support of the halogen light source extends therein. The heat resistance can be improved still further thereat via the introduction of heat conducting paste.

Particularly advantageous, from one viewpoint, is the fact that a substantially small and comparatively hot cooling body is disposed inwardly of the housing—that is, at a substantially large distance from the outer walls of the housing.

In this manner, the cooling effectiveness can be significantly improved as the cooling airflow lies then on the particularly hot surfaces. On the other hand, it is ensured that the housing, on its exterior, does not feel warm to the touch. It is particularly advantageous if the specified rate of rotation of the single or multiple fans is less than 3000 revolutions per minute and, in particular, if the noise generated by the fan operation is less than 25 decibels.

Due to the intensive cooling effect, the unit can operate with a relatively smaller rate of rotation of the fan; due to the reduced turbulence, the noise generation of the fan is clearly reduced.

The plastic or synthetic material used for the housing is not thermally loaded in that, due to its large stand-off distance from the housing-enclosed components, the housing more often tends to remain cool. It is also particularly advantageous that the back region of the housing of the light polymerization device remains cold. Heat sensitive electronic components are frequently disposed at this location as well as an LCD display whose operational temperature is significantly limited and which suffers from a reduced operational life when subjected to a raised operational temperature. Also, the storage battery power supply is not negatively influenced by the air cooling flow and it is possible to provide an adequate cooling with a comparatively small storage battery power supply accumulator in that a fan with a reduced air flow output can be deployed. In this connection, the noise emission is lowered, as well, due to the relatively small fan to, for example, 20 decibels, In accordance with the present invention, it is particularly advantageous, as well, that heat transfer to the cooling body is effected in a targeted manner from the hottest locations—and exclusively from the hottest location. This means that no temperature compensation within the housing occurs which would otherwise warm or heat the housing in total and, consequently, would effect a reduction of the cooling efficiency of the cooling body.

It is ensured, via the flow orientation of the cooling airflow transverse to the longitudinal direction of the hand-held device, that the dentist operating the hand-held device remains outside of the cooling airflow. The intake of air into the cooling device is, also, not performed directly from the patient toward the dentist but, rather, is performed from the side. In this manner, it is ensured that there is no direct exchange of suspended particles between the patient and the dentist due to the operation of the cooling airflow. The risk of infection is, consequently, substantially reduced without the requirement, however, that the dentist need wear a mouth protector.

The inventive transverse cooling channel can be configured in a conventional manner with suitable measures for protecting the channel against contact. For example, air slots in the housing can be provided which are aligned with the individual cooling air channels between the ribs of the cooling body.

It is also possible to integrate a grating or grill in the respective half of the housing in order to form the air intake opening or, respectively, the air outlet opening. The grating can also be configured as a removable grating in order to make possible an easy cleaning of the cooling body or, as the occasion arises, an easy cleaning of dirt from the fan.

It is particularly advantageous if the housing is configured in discrete components and, in particular, comprises an operational device which is, especially, in the form of a press button, and whose actuation permits the removal of a housing component or part in order to thereby provide access to the cooling body and/or the fan. The removal of the housing part is ensured via an easy access to the fan. Via this measure, the fan can be easily removed for cleaning or maintenance purposes.

In connection with such cleaning or maintenance, it is particularly advantageous if the electrical contacts for the fan motor can be plugged in and that, upon insertion of the fan into its working position, the respective plug and socket interconnections are automatically produced. This configuration simplifies, furthermore, the cleaning, maintenance, and/or, the exchange, of the fan, if this should be required at one time or another.

The cooling body itself protects the moisture sensitive electronic components so that, additionally, an activity such as, for example, a wiping off of the cooling ribs with a moistened rag, a dauber, or the like, is possible in a risk-free manner.

The cooling body can be configured with a fan on one side alone or on both sides; preferably, the cooling body is configured with a fan on one side only.

In accordance with the present invention, it is further advantageous if the cooling body is in relatively close and, at the same time, thermal, contact with the socket and/or with the terminal supports of the light source. For example, the cooling body can be formed in this region in a U-shape in order to thereby provide a reduced heat transfer resistance.

In accordance with the present invention, it is particularly advantageous if the suction side of the fan is provided for a free inflow with reduced flow resistance and the pressure side of the fan—in any event, measured in an enclosed pressure zone—is provided with cooling ribs. Additionally, the flow efficiency as well as the cooling efficiency is particularly favored by this configuration.

Further advantages, details, and features of the present invention are described in the following description of several embodiments of the invention with reference to the figures of the drawings.

DETAILED DESCRIPTION

Figure 1:
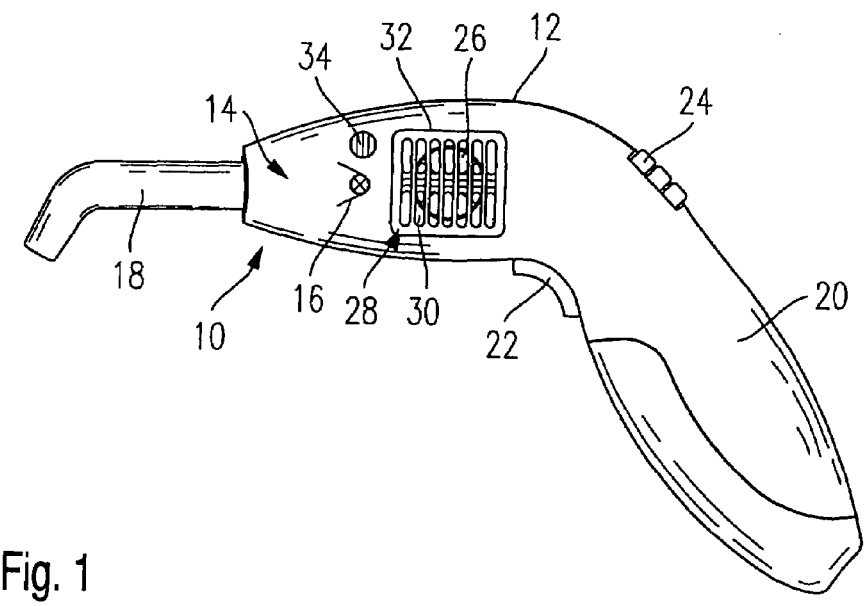
FIG. 1 is a side elevational view of a first embodiment of the light polymerization device of the present invention.

The first embodiment of the light polymerization device of the present invention illustrated in FIG. 1, designated as the light polymerization device 10, comprises a housing 12 in which a (schematically illustrated) light source 14 is mounted. The light source, which is provided with a reflector 16, emits polymerization radiation in a forward direction in the light outlet direction. The radiation passes through a light guide 18 which, in a conventional manner, has a rounded-off end.

The light polymerization device 10 comprises a hand grip portion substantially in the shape of a pistol grip. Correspondingly, a hand grip 20 is provided and the initiation of a polymerization cycle follows via actuation of a switch 22. The switch 22 is provided in the transition between the handgrip 20 and the housing 12. A program selector switch 24 is configured in opposition to the switch 22 on the opposite side of the transition between the hand grip 20 and the housing 12; the program selector switch may be optionally provided with an LCD display, as well.

In accordance with the present invention, the light polymerization device is provided with a fan 26 whose rotational axis extends transverse to the light output direction of the light source 14. The fan 26 is disposed approximately centrally in the housing 12—that is, centrally in the housing 12 itself without inclusion of the hand grip 20. The air intake and air discharge of the fan 26 is performed in a sidewise manner. As can be seen in FIG. 1, an air outlet opening 28 is provided having a plurality of air slots 30.

In the first embodiment of the light polymerization device, the air outlet opening 28 is configured in a separate housing part 32 which is in the form of a grating. Via actuation of a press button or trigger element 34, the housing part 32 can be removed so that free access can be had to the fan and a cooling body provided at the fan location and such can then be easily cleaned.

The housing 12—again, as regarded without the hand grip 20—is substantially longer than it is wide. In this manner, there is achieved a particularly pronouncedly shorter air cooling flow transversely through the housing and, as well, the total length of the device is substantially shortened.

Figure 2:
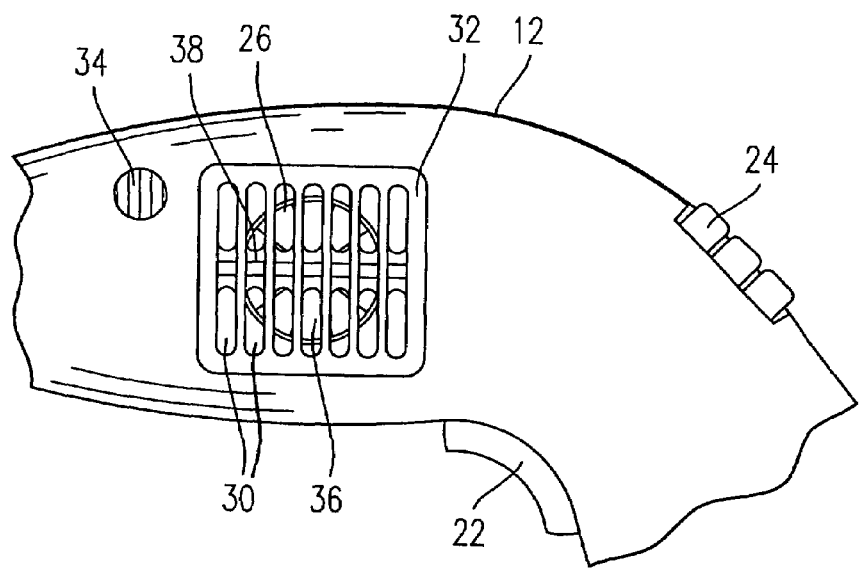
FIG. 2 is a enlarged view of the first embodiment of the light polymerization device shown in FIG. 1.

As can be seen in FIG. 2, the fan 26 is configured as an axial fan which, in conventional manner, comprises a plurality of blades 36; for example, a numerical total of 3 to 10 of such blades. As can be seen in FIG. 2, the first embodiment of the light polymerization device provides a thermal connection via circuit board 38 between the light source and a cooling body 40.

Figure 3:
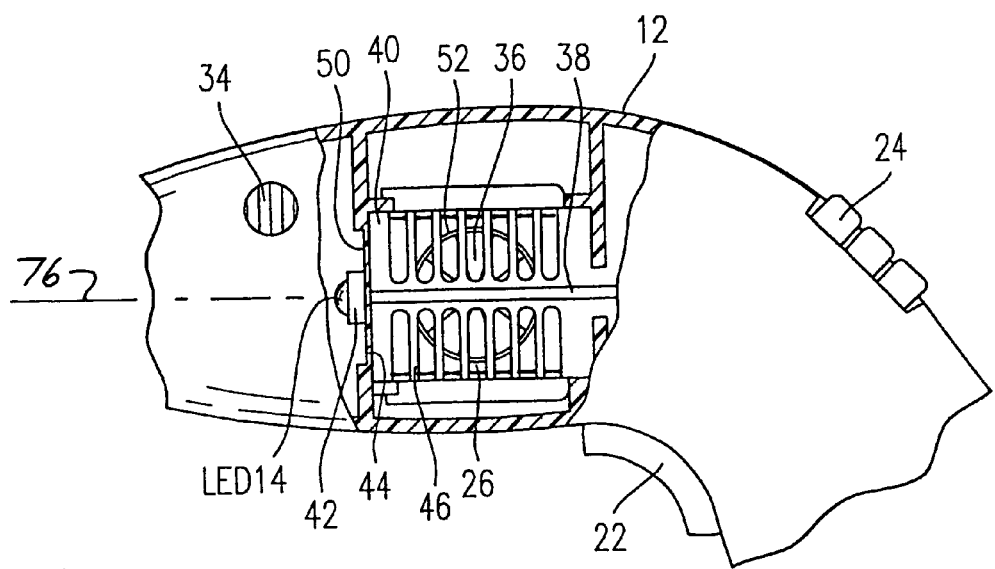
FIG. 3 is a partial cutaway sectional view of the light polymerization device shown in FIG. 2.

This circuit board 38 can be seen more clearly in FIG. 3. The cooling body is correspondingly partially transected by the circuit board 38 which extends in the longitudinal direction of the housing and supports the electrical connecting paths for the connection of the light source. The light source itself is inserted into a socket 42 which has been mounted on a printed circuit board 44. The heat outputting light source is inserted in a conventional manner into the socket 42. The heat given off by the light source is conducted away via its connection pins along a heat conducting path to the cooling body 40.

The cooling body 40 comprises a plurality of neighboring cooling ribs 46 extending parallel to one another. The cooling ribs extend outwardly from the longitudinal central axis toward the top and bottom and are oriented to the side in a manner such that they offer, in the side direction, the lowest possible flow resistance.

Figure 5:
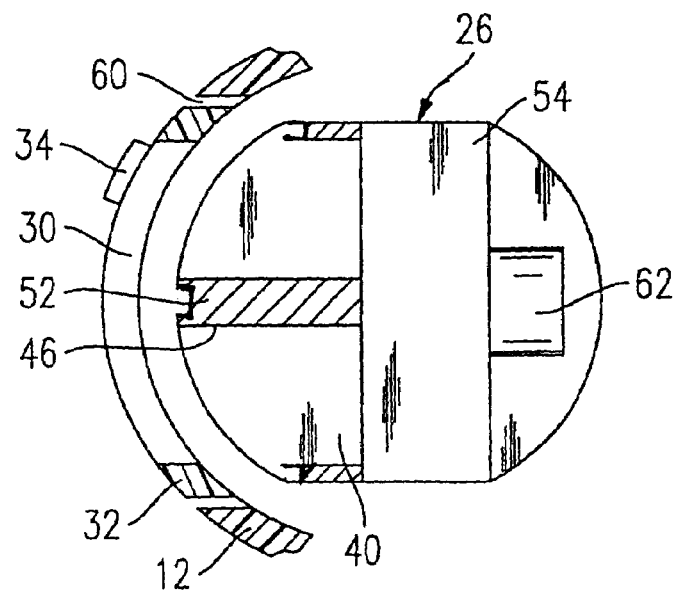
FIG. 5 is a vertical sectional view of the first embodiment of the light polymerization device shown in FIGS. 1–4.

The cooling body is, in the first embodiment of the light polymerization device, configured in a special form which can be better seen in FIG. 5. Its half cylindrical outer contour follows the contour of the interior of the housing 12 without being in actual contact therewith. The large surface configuration of the cooling ribs 46 permits a good heat transfer despite a comparatively small flow path.

Also, although a single piece cooling body is illustrated, it is to be understood, that instead of such a single piece heating body, a multiple component cooling body can also be inserted in order to facilitate the easy manufacturing of the device, whereby attention must be paid to ensure that there is only a reduced heat transfer resistance between the components of the cooling body.

As can be seen in FIG. 3, a forward end region 50 of the cooling body 40 is provided with a large material thickness. At this location, the heat of the light source is conducted to the cooling body and the enlarged material thickness makes possible a better equalization of the heat conduction.

The cooling ribs 46 are configured with substantially the same thickness and are disposed at uniform spacings from one another. Adjacent cooling ribs are connected to one another by a respective middle step 52 for both mechanical stabilization purposes as well as heat conduction purposes.

The cooling body is formed in a conventional manner of a good heat conducting material such as aluminum or an aluminum alloy.

Figure 4:
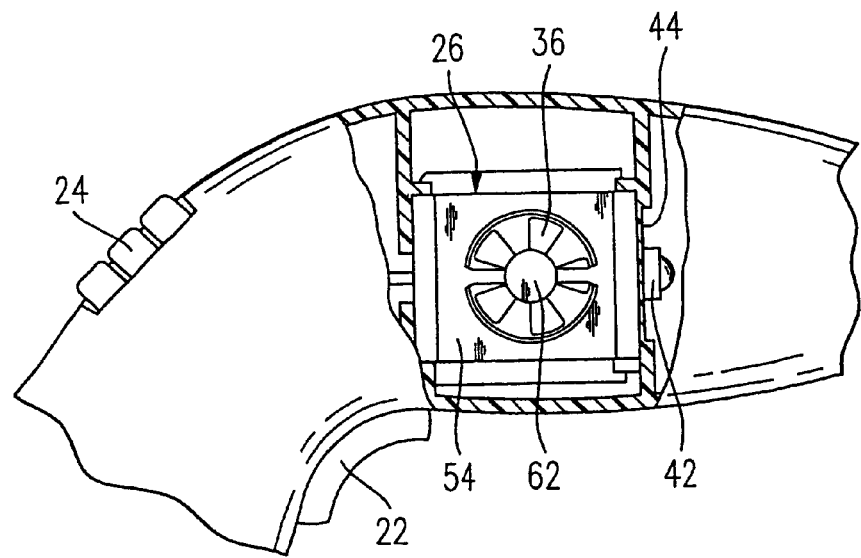
FIG. 4 is a partial cutaway sectional view of the first embodiment of the light polymerization device shown in FIGS. 1–3, whereby the side in opposition to the side shown in the views in FIGS. 1–3 is illustrated.

The cooling body forms, together with the fan 26, a compact unit which, as is shown in FIG. 4, has a fan housing 54 whose dimensions correspond to that of the cooling body 40. Preferably, the fan housing 54 and the cooling body 40 are connected to one another so that these elements can be pre-assembled as a compact unit. The fan 26 is mounted at a spacing from at least one of the cooling ribs 46.

In the illustrated embodiment, the cooling ribs 46 are provided on the air discharge side of the fan 26, whereby it is to be understood that the cooling body can, if necessary, also be disposed on the intake side of the fan or, as the occasion arises, can be disposed in an arrangement on both sides of the fan.

As can be seen in FIG. 5, the cooling body 40 extends in a contour following manner relative to the housing 12, whereby a clear gap 60 is provided which also serves to provide thermal separation.

The fan 26 is provided in a conventional manner with a fan motor 62. While the view of the fan shown in FIG. 5 only illustrates the left-hand region of the housing 12 as such would be visible upon removal of the removable housing part 32, it is to be understood that a corresponding configuration with air slots corresponding to the air slots 30 is also provided in the right-hand region of the housing.

Figure 6:
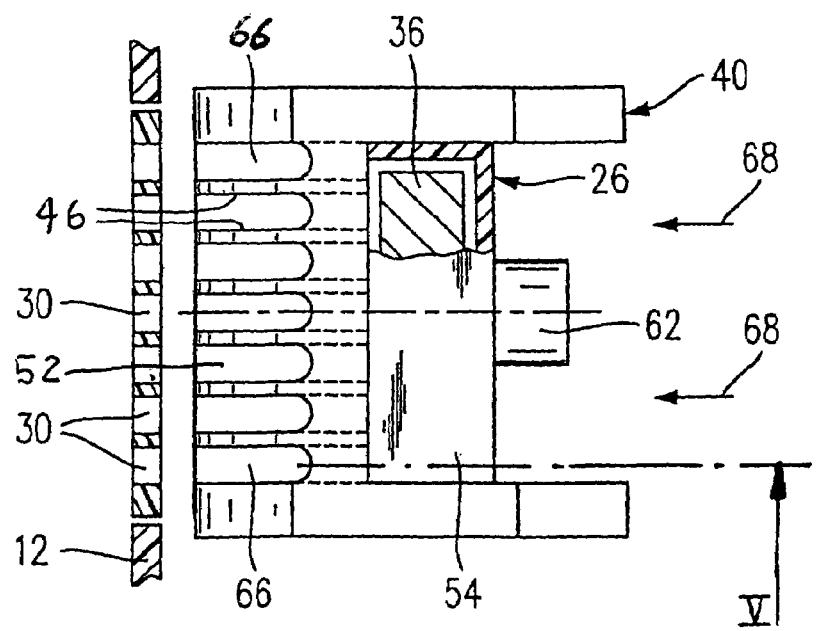
FIG. 6 is a horizontal sectional view of the first embodiment of the light polymerization device shown in FIGS. 1–5.

As can be seen in FIG. 6, the air slots 30 extend in orientations relative to individual flow channels 66. The cooling air flow extends through the housing 12 in the direction indicated by the arrows 68, whereby the inventive configuration provides a substantially large flow channel.

Figure 7:
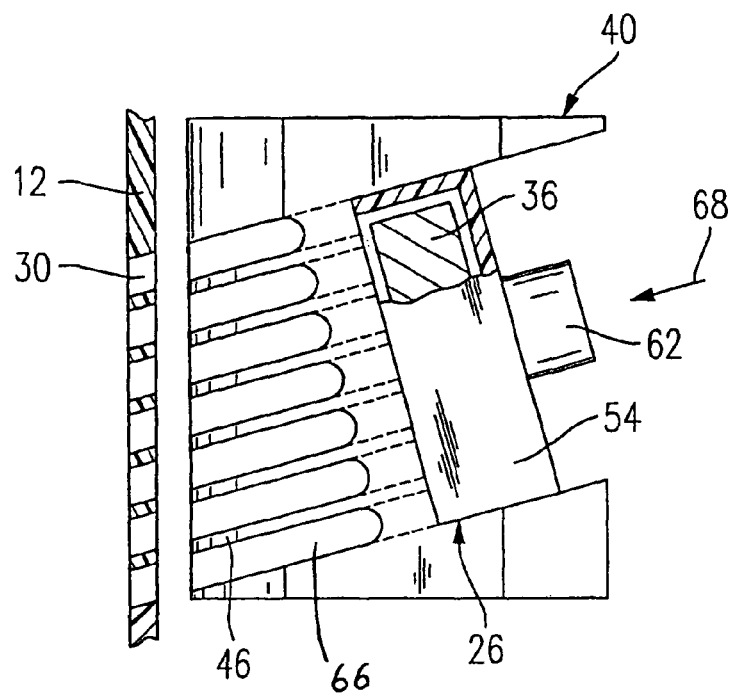
FIG. 7 is a side elevational view of a second embodiment of the light polymerization device of the present invention.

FIG. 7 illustrates a second embodiment of the light polymerization device of the present invention. In this figure, parts identical to parts identified with respect to other embodiments are denominated with the same reference numerals.

The flow direction of the flow channels 66 is, in this second embodiment of the light polymerization device, oriented at approximately an angle of 105° relative to the light output direction of the light source. The air flow of the heated cooling air is correspondingly somewhat inclined or angled toward the rear so that the diversion of the flow of the heated cooling air away from the patient is further reinforced.

It is to be understood that the flow direction of the cooling air channels can be conformed in any desired manner to the requirements.

Figure 8:
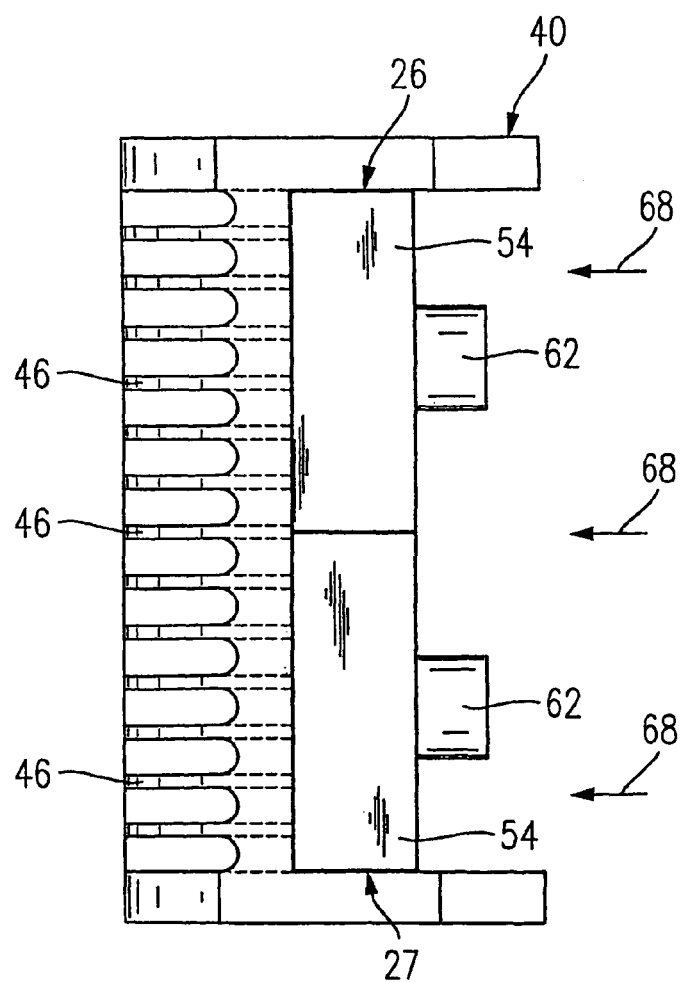
FIG. 8 is a side elevational view of a third embodiment of the light polymerization device of the present invention.

FIG. 8 illustrates a third embodiment of the light polymerization device of the present invention. In this configuration, two fans 26, 27 are provided in a serial following manner one after the other—that is, as viewed in the longitudinal direction of the housing 12—or are provided parallel to one another as viewed in the light output direction. Consequently, the cooling air flow assumes a substantially enlarged cross section and permits the deployment of a correspondingly substantially larger cooling body 40.

The third embodiment of the light polymerization device illustrated in FIG. 8 is especially suitable if a high performance light source is to be deployed, whereby, due to the enlarged cooling body, the weight of the hand-held device 10 increases.

In accordance with the present invention, it is particularly advantageous that, in the entire range of embodiments of the invention, the fan and the cooling body can be assembled together into a compact unit and, as well, are removable. Via actuation of the press button (compare as well FIG. 5), a locking mechanism is released and the unit can be removed. Also, a replacement of the one or several fans in accordance with the actual replacement requirements is easily possible. It is also possible to provide a certain spring bias in mounting the unit, whereby an automatic contacting of the unit by corresponding suitably configured contact surfaces is also possible.

Figure 9:
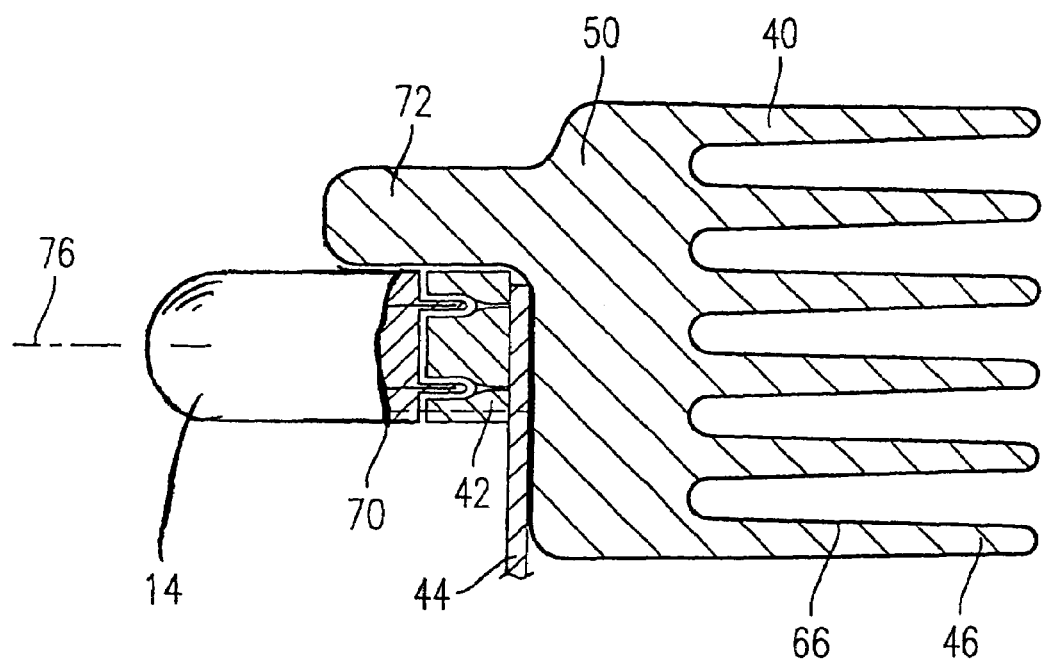
FIG. 9 is a side elevational view of a fourth embodiment of the light polymerization device of the present invention, whereby the cooling body and the light source thereof are illustrated.

FIG. 9 illustrates a fourth embodiment of the light polymerization device of the present invention characterized by an intensive contact between the heat source and the cooling body and which also permits a removal of the unit. In this connection, a portion 72 of the cooling body 40 which encircles the socket 42 and a connection support 70 of the light source 14 has a substantially U-shaped configuration.

FIG. 9 also clearly shows the orientation of the optical axis 76 of the light source 14, the optical axis extending in the light output direction. The optical axis 76 extends substantially parallel to the longitudinal axis of the housing, as viewed relative to the cylindrical portion of the housing— that is, the housing without regard to the hand grip.

As can best be seen from FIGS. 3 and 7, the rotational axis of the fan (26) is may be disposed at an angle of 60° to 90° relative to the optical axis (76). Similarly, as can best be seen from FIG. 1 the angle between the rotational axis of the fan and the longitudinal axis of the hand grip (20) is between 60° to 90°.

A printed circuit board 44 extends outwardly from the U-shaped cooling body and, in the illustrated embodiment, extends as a single piece downwardly.

It is to be understood that, as required, electronic components can be disposed as well on the cooling body, whereby it is nonetheless preferable, in this thermally loaded region, to provide solely the connector conductors and to dispose the electronics for the light polymerization device 10 in the back region of the housing 12—that is, generally between the switch 22 and the program selection switch 24.

Also, in the embodiment shown in FIG. 9, large-surface cooling ribs 46 extend outwardly from a forward end region 50, with corresponding individual flow channels 66 being formed between the cooling ribs.

In this embodiment, the cooling ribs 46 extend in a horizontal plane.

It is to be understood that the configuration of the light polymerization device can be accommodated to a wide range of requirements. For example, in order to improve the heat conduction between the socket 42 and the part 72 of the cooling body 40, a heat conducting paste can be deployed. Also, it is to be understood that, as required, an electrical insulation between the printed circuit board 44 and the cooling body can be effected.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A light polymerization device, especially a light polymerization device for polymerizing dental material, comprising:
   a housing (12) provided with a hand grip;
   a light source (14) mounted within the housing (12) and which emits polymerizing radiation along an optical axis (76);
   means for creating a flow of cooling air which moves along a path generally transverse to the optical axis (76) of the light source (14), said means including an axial fan (26) mounted within the housing, the rotational axis or the fan being at right angles to the optical axis (76); and
   a cooling body (40) which is disposed in a selected one of direct heat conducting connection and indirect heat conducting connection with the light source (14) and which is provided with cooling ribs (46) impacted by the cooling air discharged by the fan (26), a portion of the fan being received in a receptacle in the cooling body.

2. A light polymerization device according to claim 1, wherein the housing (12) has at least one air intake opening on a first side of the optical axis and at least one air exhaust opening (28) on a second side of the optical axis substantially opposed to the first side on which the air intake opening is located, the air exhaust opening (28) including air slots (30).

3. A light polymerization device according to claim 1, wherein the hand grip (20) has a longitudinal axis which extends transversely relative to the rotational axis of the fan (26).

4. A light polymerization device according to claim 3, wherein the angle between the rotational axis of the fan and the longitudinal axis of the hand grip (20) is between 60° to 90°.

5. A light polymerization device according to claim 1, wherein the cooling body (40) has a substantially cylindrical configuration.

6. A light polymerization device according to claim 5, wherein the cooling ribs (46) extend substantially parallel to the rotational axis of the fan (26).

7. A light polymerization device according to claim 1, wherein the cooling body (40) is configured on the back side thereof with end regions between which the fan (26) is received.

8. A light polymerization device according to claim 1, wherein the cooling air flow is moved through a flow channel which extends along cooling ribs (46) and the fan (26) is disposed on a selected one of the air intake side and the air discharge side of the cooling ribs (46).

9. A light polymerization device according to claim 8, wherein a selected one of a socket (42) of the light source (14) and the light source (14) itself extends into the flow channel.

10. A light polymerization device according to claim 1, wherein steps (52) are disposed along the cooling ribs (46).

11. A light polymerization device according to claim 1, wherein the housing (12) has a part (32) which is releasably mounted with respect to the remainder of the housing (12), and at least one of an air exhaust outlet (28) and an air intake opening is arranged in the part (32) of the housing (12).

12. A light polymerization device according to claim 11, wherein the fan (26) is removable once the removable part (32) of the housing (12) has been removed from the housing (12).

13. A light polymerization device according to claim 11, and further comprising a trigger element (34) disposed on the housing (12) by which the connection between the releasable part (32) of the housing (12) and the housing (12) is selectively releasable.

14. A light polymerization device according to claim 13, wherein the trigger element is a press button (34).

15. A light polymerization device according to claim 1, wherein one or more additional fans (26) are arranged along a selected one of the optical axis (76) of the light source (14) and along a longitudinal axis of the hand grip (20), the fans having rotational axes extending substantially parallel to one another.

16. A light polymerization device, especially a light polymerization device for polymerizing dental material, comprising:
    a housing;
    a light source mounted within the housing and which emits polymerizing radiation along an optical axis;
    a fan installed in the housing for creating a flow of cooling air which moves along a path generally transverse to the optical axis; and
    a cooling body which is disposed in a selected one of direct heat conducting connection and indirect heat conducting connection with the light source and which is impacted by the cooling air discharged by the fan.

17. A light polymerization device according to claim 16, wherein the fan is received is a receptacle in the cooling body.

18. A light polymerization device according to claim 16, wherein the cooling body is provided with cooling ribs.

* * * * *